United States Patent [19]

Menassa et al.

[11] Patent Number: 5,275,783
[45] Date of Patent: Jan. 4, 1994

[54] UNDECYLENATE DEODORANTS FOR ANIMAL MANURES

[75] Inventors: Aime Menassa, Paris; Henri Caupin, Versailles, both of France

[73] Assignees: Delta Agro Industries, Paris; Atochem, Puteaux, both of France

[21] Appl. No.: 29,915

[22] Filed: Mar. 11, 1993

Related U.S. Application Data

[63] Continuation of Ser. No. 948,619, Sep. 23, 1992, abandoned, which is a continuation of Ser. No. 630,183, Dec. 19, 1990, abandoned.

[30] Foreign Application Priority Data

Dec. 19, 1989 [FR] France .................. 89 16793

[51] Int. Cl.$^5$ ................................. A61L 9/00
[52] U.S. Cl. ........................ 422/5; 422/120; 424/76.6
[58] Field of Search ............... 422/5, 120; 428/905; 424/76.6, 76.21

[56] References Cited

U.S. PATENT DOCUMENTS

| | | | |
|---|---|---|---|
| 4,464,193 | 8/1984 | Kaneko et al. | 71/118 |
| 4,586,877 | 5/1986 | Watanabe et al. | 417/365 |
| 4,617,047 | 10/1986 | Bretzloff | 71/5 |
| 4,915,582 | 4/1990 | Nishikawa | 415/55.1 |

*Primary Examiner*—Lyle A. Alexander
*Attorney, Agent, or Firm*—Burns, Doane, Swecker & Mathis

[57] ABSTRACT

Malodorous liquid animal manures are deodorized by treating the sample with an effective deodorizing amount of at least one polyoxyalkylene ester of undecylenic acid having from 2 to 10 oxyalkylene recurring units.

9 Claims, 2 Drawing Sheets

UNDECYLENATE DEODORANTS FOR ANIMAL MANURES

This application is a continuation of application Ser. No. 07/948,619, filed Sep. 23, 1992, now abandoned, which is a continuation of application Ser. No. 07/630,183, filed Dec. 19, 1990, now abandoned.

CROSS-REFERENCE TO COMPANION APPLICATIONS

Copending applications Ser. No. 07/630,181 and Ser. No. 07/902,484, both filed concurrently herewith and both assigned to the assignee hereof.

BACKGROUND OF THE INVENTION

1. Field of the Invention

The present invention relates to the deodorization of liquid animal manures, in particular pig manure, and, more especially, to the deodorization of such manures by treating same with an effective deodorizing amount of a polyoxyalkylene ester of undecylenic acid.

2. Description of the Prior Art

The agriculture industry is a source of considerable objectionable odors, especially the animal production sector which generates a substantial amount of excrement. The porcine livestock segment itself generates large amounts of liquid manure, which, in addition to the pollution problems caused, is the source of objectionable odors both relative to breeding (collection) as well as to storage, treatment and fertilizing applications.

Presently, several deodorizing systems are used to combat such odors. These systems are designed to reduce odors, and also the particular pollutants.

Among the deodorizing techniques, filtration through bacterial beds is no longer in practical use and three systems predominate: surface aeration, air injection, methanization.

SUMMARY OF THE INVENTION

A major object of the present invention is the provision of novel technique for the deodorization of liquid manures, comprising treating such manures with an effective deodorizing amount of a polyoxyalkylene ester of undecylenic acid.

DETAILED DESCRIPTION OF THE PREFERRED EMBODIMENTS OF THE INVENTION

More particularly according to the present invention, the preferred polyoxyalkylene esters of undecylenic acid include the polyoxyethylene, polyoxypropylene and poly(oxyethylene)/(oxypropylene) esters thereof. More preferred are the polyoxyalkylene such esters containing from 2 to 10 oxyalkylene recurring units.

The deodorants according to the invention may comprise a single such ester of undecylenic acid, or a mixture thereof, and such esters may be used neat or in the form of a solution or suspension thereof, or they may be adsorbed onto any suitable support, such as, for example, clay particles.

In general, the undecylenic acid esters are effective as deodorants in very small amounts, for example on the order of 0.01% to 1% by weight relative to the weight of the manure to be deodorized.

The liquid manures may be treated with the above undecylenic acid esters, per se, or with combinations thereof including the typical adjuvants and additives, such as bacteriostatic or fungicidal agents, as well as free undecylenic acid itself.

The incorporation of undecylenic acid esters typically results in the formation, on the surface of the material to be treated, of a film that suppresses the evolution of any odors therefrom.

BRIEF DESCRIPTION OF THE FIGURES

The Figures of Drawing are graphs illustrating the effectiveness, for purposes of deodorization, of certain polyoxyethylene esters of undecylenic acid according to the invention.

On the curves, the abscissa represents the amount of the undecylenic acid ester incorporated, in percent by weight, and the ordinate the degree of the olfactory perception of the odor, with the values 1 to 6 respectively representing: none, very weak, weak, intermediate, strong and very strong.

In said Figures of Drawing, the upper curve corresponds to the odor of the manure itself and the lower curve to the odor of the ester.

Figure 1:
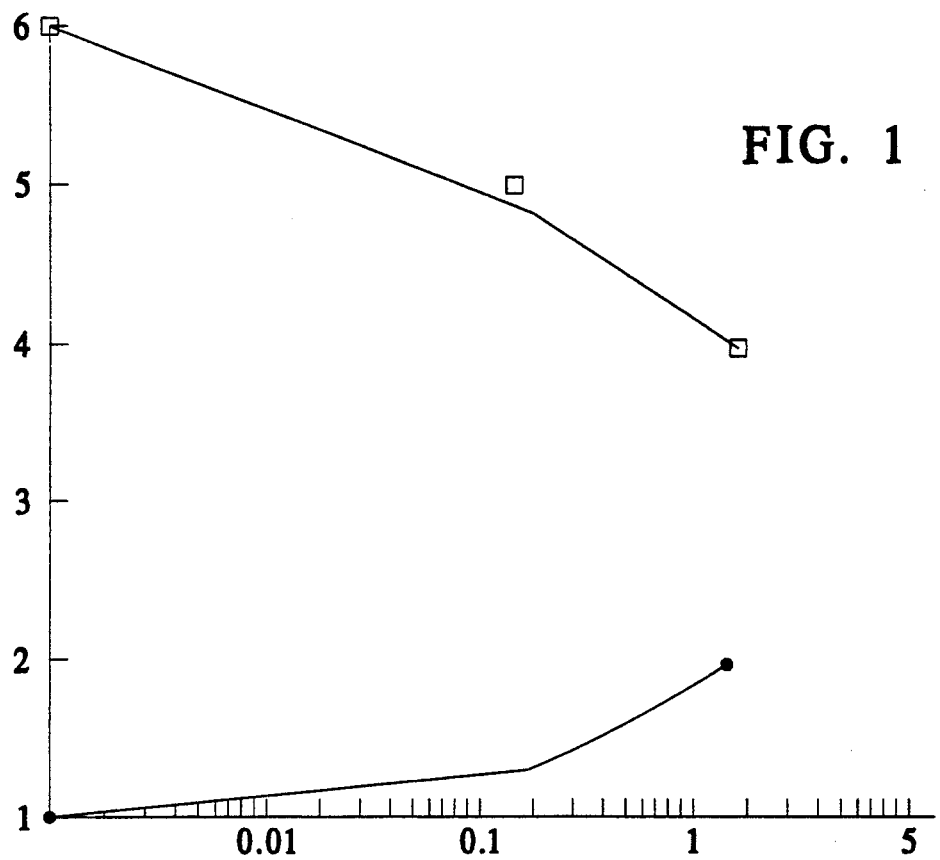
Figure 2:
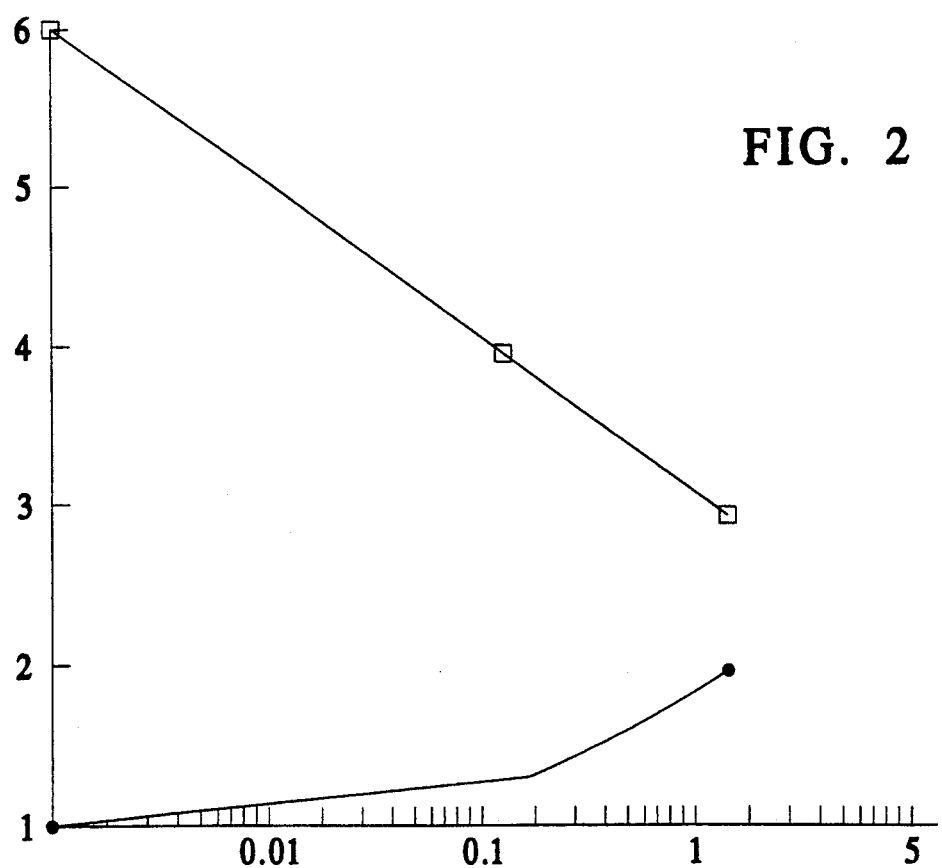

The curves of FIGS. 1 and 2, which respectively correspond to polyoxyethylene esters of undecylenic acid having 8 and 10 oxyethylene recurring units according to the invention, evidence that the reduction in the perception of the odor of the manure is not replaced appreciably by the perception of an odor emanating from the ester itself.

Figure 3:
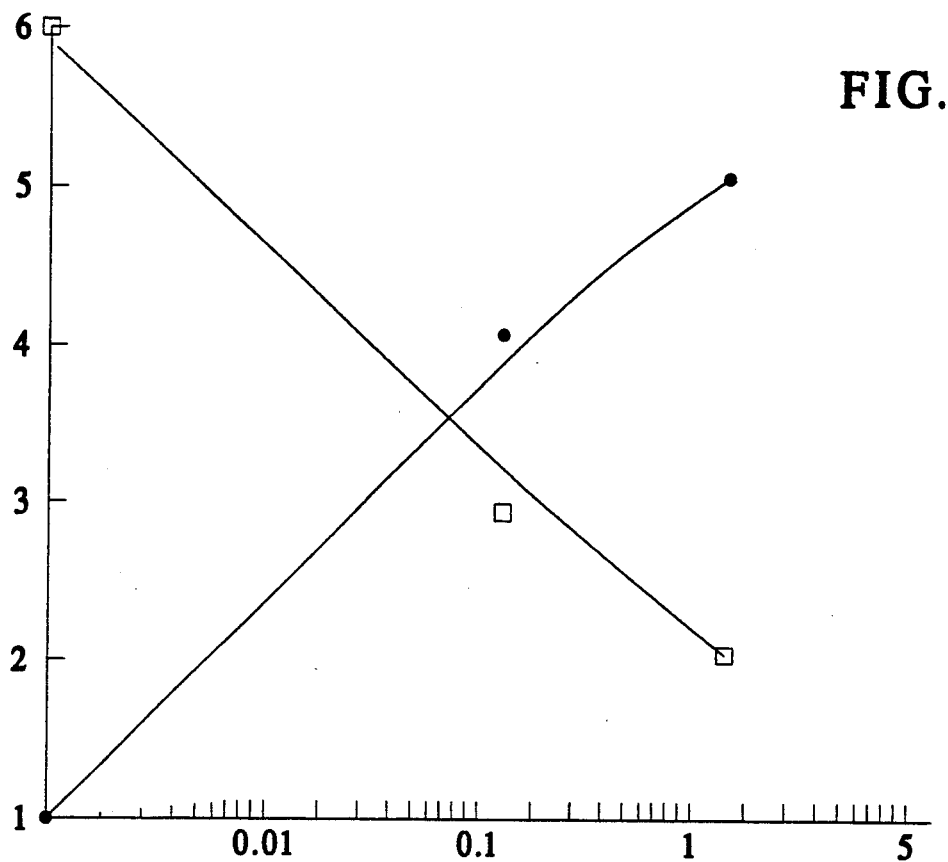
Figure 4:
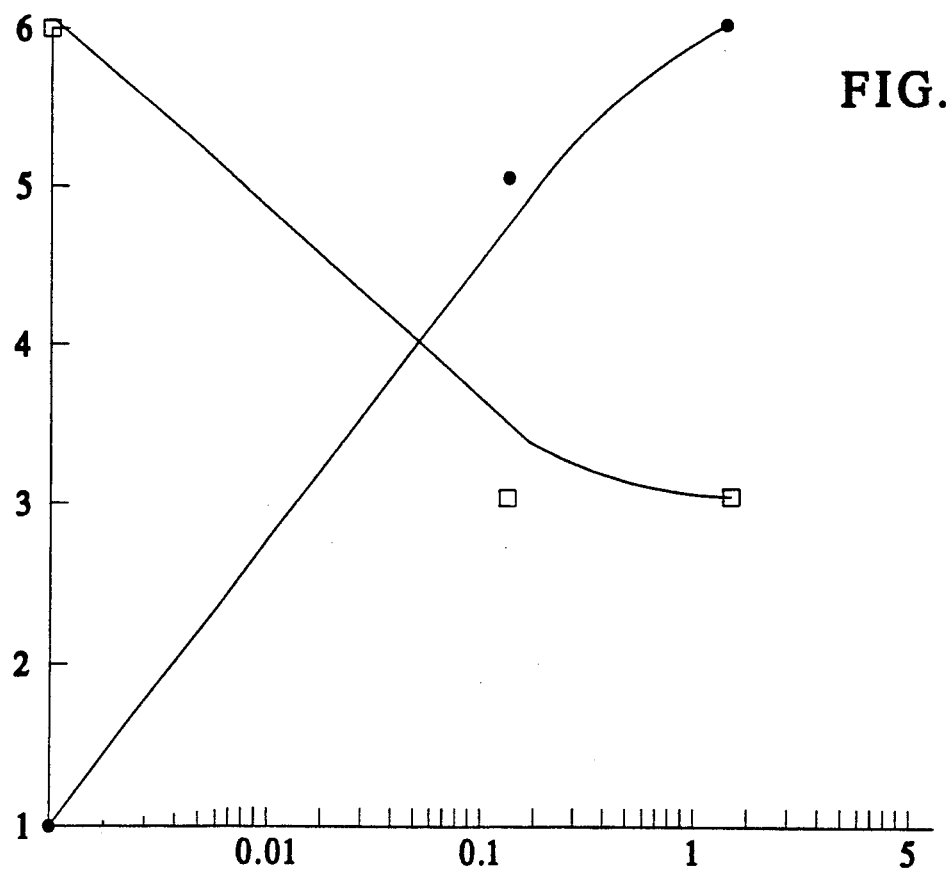

By way of comparison, FIGS. 3 and 4 respectively evidence that using methylundecylenate and the polyoxyethylene ester having 12 oxyethylene units, the reduction of the perception of the odor of the liquid manure is replaced by a strong perception of the odor of the undecylenic ester itself.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for deodorizing a malodorous liquid manure, comprising adding to a malodorous liquid manure an effective deodorizing amount of at least one polyoxyalkylene ester of undecylenic acid having from 2 to 10 oxyalkylene securing units.

2. The process as defined by claim 1, said at least one undecylenic acid ester comprising a polyoxyethylene, polyoxypropylene or poly(oxyethylene)/(oxypropylene) ester of undecylenic acid.

3. The process as defined by claim 1, comprising adding to said manure from 0.01% to 1% by weight of said at least one ester of undecylenic acid.

4. The process as defined by claim 1, comprising further adding to said manure a bacteriostatic or fungicidal agent, and/or with free undecylenic acid.

5. The process as defined by claim 1, comprising adding to said manure a liquid suspension or solution of said at least one ester of undecylenic acid.

6. The process as defined by claim 1, comprising further adding to said manure at least one ester of undecylenic acid deposited onto a support therefor.

7. The process as defined by claim 6, said support comprising clay particulates.

8. A composition of matter comprising (a) a liquid animal manure and (b) an effective manure deodorizing amount of at least one polyoxyalkylene ester of undecylenic acid having from 2 to 10 oxyalkylene recurring units.

9. The composition of matter of claim 8 wherein the effective deodorizing amount of said at least one polyoxyalkylene ester of undecylenic acid ranges from 0.01% to 1% by weight relative to the weight of the manure to be deodorized.

* * * * *